(12) United States Patent
Martin et al.

(10) Patent No.: US 9,340,820 B2
(45) Date of Patent: May 17, 2016

(54) COMPOUNDS AND METHODS FOR PROTEASE DETECTION

(75) Inventors: Stella Lorraine Martin, Ballymena (GB); Brian Walker, Newcastle (GB)

(73) Assignee: Queen's University of Belfast, Belfast (GB)

( * ) Notice: Subject to any disclaimer, the term of this patent is extended or adjusted under 35 U.S.C. 154(b) by 695 days.

(21) Appl. No.: 13/391,868

(22) PCT Filed: Aug. 26, 2010

(86) PCT No.: PCT/GB2010/051421
§ 371 (c)(1), (2), (4) Date: Mar. 7, 2012

(87) PCT Pub. No.: WO2011/024006
PCT Pub. Date: Mar. 3, 2011

(65) Prior Publication Data
US 2012/0156691 A1    Jun. 21, 2012

(30) Foreign Application Priority Data
Aug. 26, 2009  (GB) .................................. 0914883.4

(51) Int. Cl.
*C12Q 1/37*   (2006.01)
*C07F 9/6561* (2006.01)
*G01N 33/573* (2006.01)

(52) U.S. Cl.
CPC ................ *C12Q 1/37* (2013.01); *C07F 9/6561* (2013.01); *G01N 33/573* (2013.01)

(58) Field of Classification Search
CPC ....... C07F 9/6561; C12Q 1/37; G01N 33/573
USPC ........................................... 435/7.4; 548/113
See application file for complete search history.

(56) References Cited

U.S. PATENT DOCUMENTS

| 4,753,875 | A  | 6/1988  | Ryan |
| 5,290,679 | A  | 3/1994  | Terao et al. |
| 5,320,945 | A  | 6/1994  | Dessauer et al. |
| 7,232,818 | B2 | 6/2007  | Smyth et al. |
| 2005/0245435 | A1 | 11/2005 | Smyth et al. |
| 2006/0030533 | A1 | 2/2006  | Smyth et al. |
| 2006/0088471 | A1 | 4/2006  | Bennett et al. |
| 2007/0191284 | A1 | 8/2007  | Smyth et al. |
| 2007/0192882 | A1 | 8/2007  | Dewald |

FOREIGN PATENT DOCUMENTS

| AT | 70068 T | 12/1991 |
| AU | 7169787 A | 10/1987 |
| AU | 590836 B2 | 11/1989 |
| AU | 5888590 A | 1/1991 |
| AU | 622339 B2 | 4/1992 |
| AU | 2005238445 A1 | 11/2005 |
| AU | 2005243490 A1 | 11/2005 |
| AU | 2005271232 A1 | 2/2006 |
| AU | 2005295183 A1 | 4/2006 |
| BR | PI0509879 A | 10/2007 |
| CA | 2562411 A1 | 11/2005 |
| CA | 2566883 A1 | 11/2005 |
| CA | 2589765 A1 | 2/2006 |

(Continued)

OTHER PUBLICATIONS

Alterman, M. 2001. Design and Synthesis of HIV-1 Protease Inhibitors. Acta Universitatis Upsaliensis. Comprehensive Summaries of Uppsala Dissertations from the Faculty of Pharmacy 245. 70 pp. Uppsala. ISBN 91-554-4906-9.*

Gunster, Marco, "International Search Report", for PCT/GB2010/051421, as mailed Dec. 28, 2010, 6 pages.

Pan, Z, et al., "Development of activity-based probes for trypsin-family serine proteases." Bioorganic & Medicinal Chemistry Letters, vol. 16, No. 11, 2006, pp. 2882-2885.

(Continued)

*Primary Examiner* — Samantha Shterengarts
*Assistant Examiner* — John Mauro
(74) *Attorney, Agent, or Firm* — Winstead PC

(57) ABSTRACT

Alternative methods for the detection and measurement of proteases in biological samples and compounds which allow for such detection are required to allow for rapid and selective identification of these enzymes. Compounds which allow for selective identification of these enzymes are provided with assays and kits for their use.

8 Claims, 10 Drawing Sheets

FIG. 1

(56) References Cited

FOREIGN PATENT DOCUMENTS

Figure 1:
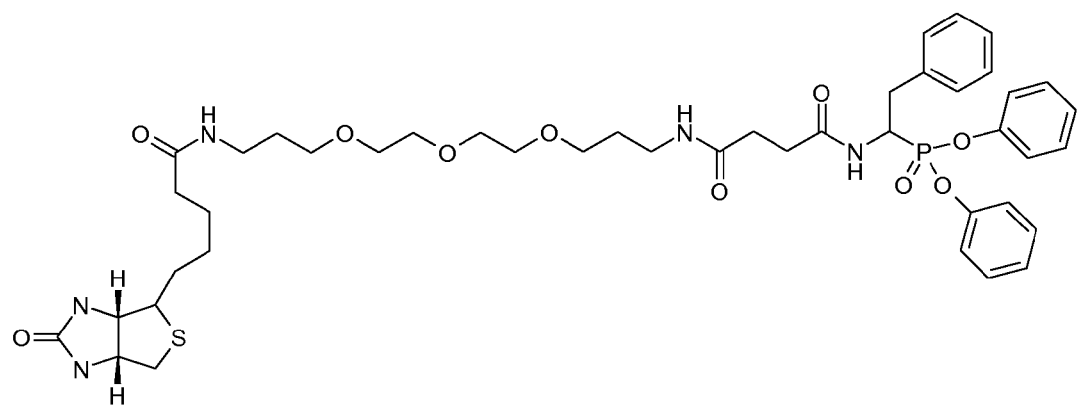

| | | |
|---|---|---|
| CA | 2584515 A1 | 4/2006 |
| CN | 101006098 A | 7/2007 |
| CN | 101044157 A | 9/2007 |
| DE | 262191 T1 | 8/1988 |
| DE | 3923340 A1 | 1/1991 |
| DE | 298444 A5 | 2/1992 |
| DK | 611387 A | 11/1987 |
| EP | 0080279 A1 | 6/1983 |
| EP | 0262191 A1 | 4/1988 |
| EP | 0396692 A1 | 11/1990 |
| EP | 0408075 A2 | 1/1991 |
| EP | 0519720 A1 | 12/1992 |
| EP | 1598428 A1 | 11/2005 |
| EP | 1745064 A2 | 1/2007 |
| EP | 1766063 A2 | 3/2007 |
| EP | 1781688 A1 | 5/2007 |
| EP | 1805208 A2 | 7/2007 |
| FI | 875151 A | 11/1987 |
| JP | 58129998 A | 8/1983 |
| JP | 2001892 A | 1/1990 |
| JP | 3053898 A | 3/1991 |
| JP | 19910146221 | 7/1992 |
| JP | 4369478 A | 12/1992 |
| JP | 7034759 A | 2/1995 |
| JP | 2560058 B2 | 12/1996 |
| JP | 2008501637 A | 1/2008 |
| KR | 20070047780 A | 5/2007 |
| NL | 8802710 A | 6/1990 |
| NO | 874734 A | 11/1987 |
| NO | 20070965 A | 4/2007 |
| WO | WO-87/05608 A1 | 9/1987 |
| WO | WO-90/05309 A1 | 5/1990 |
| WO | WO-01/36003 A2 | 5/2001 |
| WO | WO-2005/105827 A2 | 11/2005 |
| WO | WO-2005/111233 A2 | 11/2005 |
| WO | WO-2006/017842 A1 | 2/2006 |
| WO | WO-2006/045066 A2 | 4/2006 |

OTHER PUBLICATIONS

Hua, T.D., et al., "Detection of enzyme activity at trace levels; A new perspective for the direct screening of active catalytic antibodies", Tetrahedron Letters, vol. 37, No. 2, 1996, pp. 175-178.

Matsumoto, H., et al., "Design, synthesis, and biological evaluation of anti-HIV double-drugs: conjugates of HIV protease inhibitors with a reverse transcriptase inhibitor through spontaneously cleavable linkers", Bioorganic and Medicinal Chemistry, vol. 9, No. 6, 2001, pp. 1589-1600.

Walker, Brian, "Asymmetric preference of serine proteases toward phosphonate and phosphinate esters", Biochemical and Biophysical Research Communications, vol. 276, No. 3, 2000, pp. 1235-1239.

Gilmore, Brendan F., et al., "Synthesis, kinetic evaluation, and utilization of a biotinylated dipeptide proline diphenyl phosphonate for the disclosure of dipeptidyl peptidase IV-like serine proteases", Biochemical and Biophysical Research Communications, vol. 347, No. 1, 2006, pp. 373-379.

Hawthorne, S., et al., "Utilization of biotinylated diphenyl phosphonates for disclosure of serine proteases", Analytical Biochemistry, vol. 326, No. 2, 2004, pp. 273-275.

Gilmore, B.F., et al., "Dipeptide proline diphenyl phosphonates are potent, irreversible inhibitors of seprase (FAPalpha)", Biochemical and Biophysical Research Communications, vol. 346, No. 2, 2006, pp. 436-446.

Gilmore, Brendan F., "Expedited solid-phase synthesis of fluorescently labeled and biotinylated aminoalkane diphenyl phosphonate affinity probes for chymotrypsin- and elastase-like serine proteases", Bioconjugate Chemistry, vol. 20, No. 11, Nov. 2009, pp. 2098-2105.

Abuelyaman, Ahmed S., et al., "Synthesis and Kinetic Studies of Diphenyl 1-(N-Peptidylamino)alkanephosphonate Esters and Their Biotinylated Derivatives as Inhibitors of Serine Proteases and Probes for Lymphocyte Granzymes", Archives of Biochemistry and Biophysics, vol. 344, No. 2, 1997, pp. 271-280.

Cox, S.W, et al., "A Simple, Combined Fluorogenic and Chromogenic Method for the Assay of Proteases in Gingival Crevicular Fluid", J Periodont Res, vol. 25, 1990, pp. 164-171.

Eley, B.M., et al., "Advances in Periodontal Diagnosis 8. Commercial Diagnostic Kits Based on GCF Proteolytic and Hydrolytic Enzyme Levels", British Dental Journal, vol. 184, No. 8, Apr. 25, 1998, pp. 373-376.

Oleksyszyn, Jozef, et al., "Amino Acid and Peptide Phosphonate Derivatives as Specific Inhibitors of Serine Peptidases", Methods in Enzmology, vol. 244, 1994, pp. 423-441.

Hamilton, Robert, et al., "A Convenient Synthesis of N-Protected Diphenyl Phosphonate Ester Analogues of Ornithine, Lysine and Homolysine", Tetrahedron Letters, vol. 34, No. 17, 1993, pp. 2847-2850.

Oleksyszyn, Jozef, et al., "Irreversible Inhibition of Serine Proteases by Peptide Derivatives of ($\alpha$-Aminoalkyl) Phosphonate Diphenyl Esters", Biochemistry, vol. 30, 1991, pp. 485-493.

Hamilton, Robert, et al., "A Convenient Synthesis of Phosphonate Isosteres of Serine Phosphates", Tetrahedron Letters, vol. 35, No. 21, 1994, pp. 3597-3600.

Djekic, Uros V., et al., "Attacking the Multi-Tiered Proteolytic Pathology of COPD: New Insights from Basic and Translational Studies", Pharmacology & Therapeutics, vol. 121, 2009, pp. 132-146.

Mayer-Hamblett, Nicole, et al., "Association between Pulmonary Function and Sputum Biomarkers in Cystic Fibrosis", American Journal of Respiratory and Critical Care Medicine, vol. 175, 2007, pp. 822-828.

Gaetani, Paolo, et al., "Collagen Cross-Linkage, Elastolytic and Collagenolytic Activites in Cerebral Aneurysms: A Preliminary Investigation", Life Sciences, vol. 63, No. 4, 1998, pp. 285-292.

Hawthorne, S.J., et al., "Identification and Characterization of the Cysteine and Serine Proteinases of the Trematode, *Haplometra Cylindracea* and Determination of Their Haemoglobinase Activity", Parasitology, vol. 108, 1994, pp. 595-601.

Tsang, Kenneth W., et al., "Sputum Elastase in Steady-State Bronchiectasis", Chest, vol. 117, No. 2, 2000, pp. 420-426.

Hamilton, Robert, et al., "Synthesis and Proteinase Inhibitory Properties of Diphenyl Phosphonate Analogues of Aspartic and Glutamic Acids", Bioorganic & Medicinal Chemistry Letters, vol. 8, 1998, pp. 1655-1660.

Henriksen, Peter A., et al., "Human Neutrophil Elastase: Mediator and Therapeutic Target in Atherosclerosis", The International Journal of Biochemistry & Cell Biology, vol. 40, 2008, pp. 1095-1100.

Sato, Takashi, et al., "Neutrophil Elastase and Cancer", Surgical Oncology, vol. 15, 2006, pp. 217-222.

Ozcaka, O., et al., "Smoking and Matrix Metalloproteinases, Neutrophil Elastase and Myeloperoxidase in Chronic Periodontitis", Oral Diseases, vol. 17, 2011, pp. 68-76.

Fujimoto, K., et al., "Airway Inflammation during Stable and Acutely Exacerbated Chronic Obstructive Pulmonary Disease", European Respiratory Journal, vol. 25, No. 4, 2005, pp. 640-646.

Trengove, Naomi J., et al., "Analysis of the Acute and Chronic Wound Environments: The Role of Proteases and their Inhibitors", Wound Repair and Regeneration, vol. 7, No. 6, 1999, pp. 442-452.

Paliouras, Miltiadis, et al., "Human Tissue Kallikreins: The Cancer Biomarker Family", Cancer Letters, vol. 249, 2007, pp. 61-79.

Hamilton, Robert, et al., "A Highly Convenient Route to Optically Pure $\alpha$-Aminophosphonic Acids", Tetrahedron Letters, vol. 36, No. 25, 1995, pp. 4451-4454.

Hawthorne, Susan, et al., "Utilization of Biotinylated Diphenyl Phosphonates for Disclosure of Serine Proteases", Analytical Biochemistry, vol. 326, 2004, pp. 273-275.

Hayakawa, Mineji, et al., "Sivelestat (Selective Neutrophil Elastase Inhibitor) Improves the Mortality Rate of Sepsis Associated with Both Acute Respiratory Distress Syndrome and Disseminated Intravascular Coagulation Patients", Shock, vol. 33, No. 1, 2010, pp. 14-18.

Pan, Zhengying, et al., "Development of Activity-Based Probes for Trypsin-Family Serine Proteases", Bioorganic & Medicinal Chemistry Letters, vol. 16, 2006, pp. 2882-2885.

(56) References Cited

OTHER PUBLICATIONS

Kay, Gillian, et al., "The Detection of Serine Elastase in Human Breast Cancer", Biochemical Society Transactions, vol. 22, 1993, p. 20S.

Frossard, Jean-Louis, et al., "New Serum Markers for the Detection of Severe Acute Pancreatitis in Humans", American Journal of Respiratory and Critical Care Medicine, vol. 164, 2001, pp. 162-170.

Walker, Brian, et al., "Asymmetric Preference of Serine Proteases toward Phosphonate and Phosphinate Esters", Biochemical and Biophysical Research Communications, vol. 276, 2000, pp. 1235-1239.

Loos, Bruno G., et al., "Host-Derived Diagnostic Markers for Periodontitis: Do They Exist in Gingival Crevice Fluid?", Periodontology, vol. 39, 2005, pp. 53-72.

* cited by examiner r = 0.992 (p=0.000)

Fig. 12

A

| Sample | Method of analysis | NE Activity (mg/ml) | |
|---|---|---|---|
| | | Mean (SD) | Median (IQR) |
| PBS Wash | Fluorescence | 120.1 (131.9) | 63.3 (2.5 – 229.1) |
| | NE-Tag | 113.6 (274.6) | 1.78 (0.54 – 93.7) |
| | InnoZyme | 116.2 (281.3) | 17.7 (6.87 – 46.8) |
| Neat sol | Fluorescence | 411.9 (615.5) | 44.7 (0.10 – 660.3) |
| | NE-Tag | 81.7 (333.4) | 0.40 (0.31 – 0.90) |
| | InnoZyme | ND | ND |

B

| Method of analysis | Fluorescence Activity Assay | NE-Tag ELISA |
|---|---|---|
| Fluorescence | | |
| PBS wash | - | 0.330 (0.027) * |
| Neat sol | - | 0.815 (0.000) ** |
| NE-Tag ELISA | | |
| PBS wash | 0.330 (0.027) * | - |
| Neat sol | 0.815 (0.000) ** | - |
| InnoZyme | | |
| PBS wash | 0.259 (0.085) | 0.910 (0.000) ** |
| Neat sol | ND | ND |

| Parameter | Fluorescence Activity Assay r value (p) | NE-Tag ELISA r value (p) | InnoZyme r value (p) |
|---|---|---|---|
| Age | -0.204 (0.178) | 0.024 (0.876) | -0.047 (0.759) |
| BMI | -0.085 (0.579) | -0.045 (0.768) | 0.113 (0.461) |
| FEV1 (%) | 0.180 (0.236) | -0.313 (0.036) * | -0.384 (0.009) ** |
| FVC (%) | 0.243 (0.121) † | -0.228 (0.147) † | -0.142 (0.369) † |
| Serum CRP | -0.247 (0.102) † | 0.314 (0.035) † * | 0.245 (0.105) † |
| Total WCC | -0.209 (0.168) | 0.554 (0.000) ** | 0.493 (0.001) ** |
| Total neutrophils | -0.238 (0.115) | 0.566 (0.000) ** | 0.514 (0.000) ** |

Fig. 13

COMPOUNDS AND METHODS FOR PROTEASE DETECTION

FIELD OF THE INVENTION

The present invention relates to methods and compounds for targeting biomarkers, particularly active proteases, e.g. active serine proteases. Furthermore, the present invention relates to using such compounds in the detection and/or inhibition of biomarkers, a method of detecting a pathological condition, for example inflammation, and to a kit comprising such compound.

BACKGROUND OF THE INVENTION

Serine proteases are one of the most widely studied classes of enzymes: this is largely due to their well-characterised, widespread and diverse roles in a host of physiological and pathological processes. Many disorders are caused by a dysfunction in the normal exquisite regulation of the activity of these proteolytic enzymes, resulting in abnormal tissue destruction and/or aberrant processing of other proteins and peptides. For example, the activity of the serine protease neutrophil elastase (NE), is normally tightly controlled by a variety of native inhibitors such as alpha$_1$ antitrypsin (AAT), secretory leukocyte protease inhibitor (SLPI) and elafin; however, in chronic inflammation such as that found within the lung in cystic fibrosis (CF), this protease overwhelms the tissues natural defences, and the resulting unchecked activity is implicated in tissue destruction, an impaired immune response and ultimately pulmonary decline. Indeed, NE as a biomarker of infection and inflammation has been shown to correlate with the severity of several other respiratory diseases such as chronic obstructive pulmonary disease (COPD) and bronchiectasis (Mayer-Hamblett et al., 2007; Fujimoto et al., 2005; Tsang et al., 2000).

NE has also been found to be elevated in gingival crevice fluid and therefore has value as a biomarker of periodontal disease (Loos and Tjoa, 2005).

Serine proteases have also been implicated as biomarkers in a variety of cancers. For example, human tissue kallikreins (KLKs) which represent the largest group of serine proteases and of which prostate specific antigen (PSA) is the most well known, have attracted particular attention as biomarkers for the screening, diagnosis, prognosis and monitoring of malignant disease (Paliouras et al., 2007). Other serine proteases implicated in tumour-associated events, such as angiogenesis, invasion and metastasis include urokinase and tissue plasminogen activators.

Currently, active proteases are measured predominantly using either chromogenic or fluorogenic substrates which require technical expertise and expensive instrumentation. In addition, these substrates lack selectivity when used with crude biological samples containing a battery of enzymes with multiple proteolytic and hydrolytic proteases. These assays require samples to be processed, which entails the use of expensive instrumentation.

Other methods of detection include immunoassays which are time and labour intensive and due to their expense, require samples to be batched for analysis resulting in long-term storage of samples and the negative impact of freeze/thaw cycles on protein integrity. In addition these assays only measure total protein and cannot differentiate between active and latent enzymes.

Therefore, due to the lack of a rapid and user-friendly detection system, proteases cannot be assayed in the clinic and are rarely assayed in hospital laboratories.

Indeed, although the importance of NE in the pathogenesis of neutrophilic respiratory disease has been established and there is an understanding that routine NE assessment in the clinic would provide important biochemical information which would assist in patient management, NE is only measured in airway samples as an endpoint in research studies and in clinical trials assessing the efficacy of therapeutic interventions. In these cases samples are transferred to contract research laboratories for processing, storage and subsequent analysis.

Up until the early 1990's, research into the association of NE with periodontal disease included placing strips containing a fluorogenic substrate (Prognostiks, Dentsply), directly into the gingival crevice (Eley and Cox, 1998). Fluorogenic substrates used include MeOSuc-Ala-Ala-Pro-Val-7-amidotrifluoro-methylcoumarin (AFC), which was developed by Enzyme System Products (now MP Biomedicals) for Dentsply. This method was not sufficiently sensitive and was also inconvenient for a patient. Another assay system, again based on the fluorogenic substrate detailed above and impregnated into discs, was not commercially developed (Cox et al., 1990).

Other methods currently available to measure proteases such as NE are in ELISA (Enzyme linked Immuno Sorbent Assay) format. For example, in order to measure NE, a NE-alpha$_1$ antitrypsin complex (AAT or $\alpha_1$PI) (Bender Medsystems and Biovendor) is determined. AAT is the endogenous inhibitor of NE, and in normal conditions an amount of NE-AAT correlates with an amount of released NE. In neutrophilic diseases however, AAT is overwhelmed by the excessive burden of NE, and free active NE can be measured compared to healthy individuals, where no activity can be detected due to effective inhibition. Measurement of NE-AAT complexes alone would therefore only give an indication of inhibited NE, which, as it is already sequestered, cannot cause damage to the surrounding tissue environment, whether it be the gums in dental disease or the lungs in CF. The important measurement has to be that of the unchecked elastinolytic activity. This is well documented in the literature.

Calbiochem currently offer an active NE ELISA on the market in the form of the Innozyme™ NE Immunocapture activity assay kit. By utilising a monoclonal capture antibody to NE, lack of specificity of the subsequent substrate step is compensated for, as the remainder of the crude sample is removed by washing. The major drawback is that the substrate step requires a minimum incubation period of 4 hours up to 24 hours at 37° C., which makes this assay time consuming and impractical for use, particularly in the clinic or hospital laboratories.

Phosphonate probes have been previously reported to target the serine hydrolase family, and selective probes that specifically target the trypsin-like serine protease based on diphenyl phosphosate (DPP)-derived probes have been developed (Hawthorne et al., *Anal. Biochem.* 326 (2004) 273-275; Pan et al, Bioorg. Med. Chem. Lett. 16 (2006) 2882-2885). However, alternative probes would be useful to aid a better understanding of the activity of protease enzymes in samples to be tested and assays in this regard.

SUMMARY OF INVENTION

The inventors have developed biomarker-specific compounds and novel and rapid methods for targeting, i.e. detecting and/or inhibiting, biomarkers in a wide variety of samples having different complexities, particularly biomarkers being active proteases such as active serine proteases. Such biomarkers are of diagnostic and prognostic value, for example for detecting a pathological condition such as inflammation.

In particular, the compound is capable of stably binding active target protease species, thereby tagging the target proteases present, for example in complex mixtures comprising various protein species, such as sputum sol, bronchoalveolar lavage, and fluids from sites of inflammation or the like.

According to a first aspect of the invention there is provided a compound, for detection and/or inhibition of a specific biomarker in a sample, wherein the compound comprises:
a binding group capable of stably binding the biomarker,
a specific recognition group for the biomarker,
a spacer group,
a succinyl moiety, and
a reporter group.

Advantageously, in embodiments, the succinyl moiety can link the recognition group and the spacer group. Whilst the inventors do not wish to be bound by theory, the succinyl moiety advantageously is believed to act as a second recognition group for the specific biomarker. In particular, it is believed to facilitate the formation of essential H-bonding interactions between the compound and the biomarker, for example the protease by virtue of the amide bond formed between the amino functionality of the diphenyl phosphonate and one its two-carboxyl functionalities.

It can also act as a spacer unit to facilitate the interaction between for example the streptavidin-HRP conjugate and the biotin moiety so as to improve the 'signal to noise ratio' of the assay.

Additionally, the succinyl moiety or group may allow the compound of the present invention to be generated on a solid phase compared to generation in solution. The ability of the compounds of the present invention to be formed on a solid phase provides an important advantage over compounds used to assay for biomarkers which may only be formed in solution.

In particular, it is believed to make possible the solid phase synthesis of the desired active site-directed activity compounds, including the 'on-resin' derivatization with the biotin reporter group and the incorporation of the pegylated spacer unit. The solution phase incorporation of biotin into peptides is often slow and necessitates the use of excess biotin to drive the reaction to completion. This, in turn, means that extensive purification is needed to obtain the desired product free from contaminating, unbound biotin. The omission of the succinyl moiety would preclude anchoring of the diphenyl phosphonate to the solid phase support, thus removing the option for the expedited solid phase synthesis of the compound.

The succinyl moiety may bind the specific biomarker in particular where the biomarker is a protease, preferably the active seine protease. Further, the succinyl renders the activity probe more resistant to degradation by peptidases that are present in the biological matrices on which the protease assays, for example neutrophil elastase assays, are being performed. Peptidases are known to be highly efficient in the degradation of peptides composed entirely of alpha amino acids. Their degradative action is greatly reduced when the peptide contains a non-proteogenic amino acid such as homo-beta amino acids. The succinyl moiety differs from an alpha amino acid in two important respects it does not contain a NH— function, neither does it have a recognisable alpha carbon since it is more structurally analogous to a homo-beta amino acid.

In embodiments, the succinyl moiety can be OCCH$_2$CH$_2$CO. The compounds of the present invention may be prepared by reacting, for example succinic anhydride to the amino portion of the amino acid of the specific recognition group to form succinyl derivatives such that when linked the linking portion of the specific binding group and the spacer group may be represented by

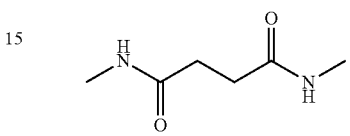

As will be appreciated, during synthesis of the compounds, the succinylated binding and recognition group is brought into contact with the spacer group, for example the PEG group, to allow reaction. This can form the connection between the recognition and the spacer groups.

Typically the biomarker is a protease, in particular an active serine protease. Typically the serine protease may be an elastase-like protease, for example neutrophil elastase (NE) or similar, a trypsin-like protease, for example the majority of KLKs, or a chymotrypsin-like protease, for example PSA, KLK-7 and KLK-9 or similar. According to one embodiment, the serine protease may be a neutrophil-derived protease such as neutrophil elastase, cathepsin G, proteinase-3 or similar. Preferably, the serine protease is NE.

Whilst Chloromethylketone-derivatives have previously been reported as useful serine protease inhibitors, in contrast to the compounds of the present invention chloromethylketone-derivatives exhibit a lack of specificity and high instability.

Advantageously the compounds of the present invention can be highly specific for a biomarker to be detected. In addition, the compounds of the present invention can be potent at micromolar concentrations, stable in solution, even at room temperature, and have an extended shelf life. This allows for robust, reliable testing, resulting in highly reproducible results. The compounds of the present invention can have high specificity and stability. Furthermore, the compounds of the present invention can be capable of functioning as time-dependent, irreversible inhibitors of biomarkers, in particular protease biomarkers.

Typically in a preferred embodiment a compound of the present invention comprises a reporter group linked to the succinyl moiety by a spacer group. The succinyl moiety is linked to the specific recognition group which is linked to the binding group. In preferred embodiments, the various groups are linked directly. This arrangement is preferably for both efficient capture of the protease and disclosure/detection of the reporter group. Without wishing to be bound by theory, any other combinations/linkages are considered to compromise the capture and the disclosure of the protease biomarker. In the present specification the terms "succinyl moiety" and "succinyl group" can be used interchangeably.

According to a one embodiment, the succinyl moiety links the recognition group and the spacer group. The succinyl moiety is highly preferred in order to allow the compound of the present invention to be generated on a solid phase compared to generation in the more chemically difficult solution phase. The succinyl moiety can provide a point of attachment between the specific recognition group of the inhibitor, and the amino linker group which is present on many resins which would typically form the solid phase. The ability of the compounds of the present invention to be formed on a solid phase provides an important advantage over compounds used to assay for biomarkers which may only be formed in solution. The provision of the succinyl group in the compounds of the present invention means that the synthesis of the compounds is typically expedited.

The binding group selectively binds the biomarker, for example the protease. Typically the binding group may be an aminophenylphosphinate group or a diphenylphosphonate group. Such a binding group generally selectively binds an active biomarker through the exploitation of its inherent catalytic activity. It will be appreciated that such groups may be able to irreversibly covalently attach to the biomarker (in particular the protease biomarker), and may thereby clearly discriminate between active and inactive proteases.

Advantageously, the compound of the present invention comprising a diphenylphosphonate or monophenylphosphinate binding group lacks the ability to bind to proteins other than the target biomarker, i.e. collateral proteins residing in the sample, and accordingly the compound of the present invention provides a pronounced inhibitory activity with respect to the biomarker exclusively, in particular the active serine protease biomarker.

Advantageously, in embodiments the binding group can comprise a monophenylphosphinate group.

If the binding group is a monophenylphosphinate group, the compound of the present invention will exhibit chirality. The compound may be an (R) and (S) epimer as there are several options for the location of the reporter group or groups (see FIG. 4). Previously, racemic compounds were employed since synthetic methodologies were unable to achieve chiral induction. This was a drawback since the (R) and (S) epimers (with respect to the configuration of the α-carbon) of such derivatives may exhibit differing inhibitory activities. The inventors have now shown that where the compound of the present invention comprises a monophenylphosphinate binding group, the (R)-conformer possesses superior inhibitory activity. A warhead providing such activity was discussed in Walker et al., 2000. In embodiments, the binding group can be an R-confirmer of monophenyl-phosphinate. Furthermore, the phosphinate analogue exhibits improved properties compared to its diphenylphosphonate counterpart in activating its target biomarker. A monophenylphosphinate binding group will therefore also be a useful entity for the incorporation into the probe construct.

According to one embodiment of the present invention, the specific recognition group can be a peptidyl group for example, amino acids positioned at a P1 and/or P2 position as known conventionally in the art etc. Preferably, where the target biomarker is NE the peptidyl group can be a Valyl group; where the target biomarker is a chymotrypsin-like protease the peptidyl group can be a Phenylalanyl group; and where the target biomarker is a trypsin-like or kallikrein proteases the peptidyl group can be a Lysyl or Arginyl group. As will be appreciated, other peptidyl groups can be present at $P_1$ or $P_2$ (or $P_1'$ or $P_2'$ in the case of monophenylphosphinates) to increase specificity. It will be appreciated that the peptidyl group can be selected based on known information regarding subsite specificities of proteases, e.g. Valyl-prolyl-valyl for elastase.

The specific recognition group, allowing for elaboration of $P_2$-$P_3$ specificities, can be connected to the binding group via any suitable chemical bond. Where the binding group is a monophenylphosphinate group or diphenylphosphonate group, the specific recognition group is typically connected to the binding group via a phenyl ester.

The reporter group can be any group that can be directly or indirectly detected, for example physically, chemically and/or biochemically. Particularly, it may be any suitable chemical residue, group, hapten or antigen. For example, the reporter group may comprise biotin, 2,4-dinitrophenol, or a derivative thereof, or one or more hapten(s) or antigen(s).

In a preferred embodiment the reporter group can comprise a biotin moiety. As will be appreciated, the biotin moiety can specifically be captured by streptavidin. Additionally, streptavidin may be immobilised onto a suitable solid matrix, which may be in the form of a plate, bead, film, membrane, sheet, chip, disc, array, nanoparticle, carbon nanotube or similar. The matrix may be formed from a material selected from plastics, glass, metal, agarose, nitrocellulose, polymer, silicon (wafer), carbon or the like.

Alternatively, the reporter group may comprise a 2,4-dinitrophenyl moiety, which may be detected by a corresponding antibody, or the reporter group may comprise a suitable hapten or antigen, e.g. His-Tag, FLAG-Tag, ferrocene, rhodamine, texas red, green fluorescent protein (GFP), glutathione S-transferase (GST) or similar, which may be detected by a corresponding antibody. As will be appreciated by a person of ordinary skill in the art any suitable conventional reporter group may be used. In embodiments, a compound of the invention may comprise more than one reporter group of the same or different type.

Alternatively, compounds of the invention with specificity to different proteases, may be provided with respect to a reporter group, such that a test sample can be probed using multiple different compounds of the invention to detect different proteases present in a sample at the same time.

According to a further embodiment, the spacer group may comprise at least one polyethylene glycol (PEG) residue, suitably more than one PEG residue.

Where the spacer group comprises one or more PEG residues the spacer group may have a structure as shown in FIGS. 1-5. In embodiments, the one or more PEG residues can have the structure

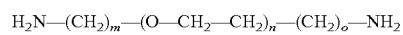

where n=1, 2, 3, 4, 5, 6, and m and o are independently selected from 1-6 etc.

In embodiments the spacer can be an amino derivatized PEG, for example selected or derived from:
8-amino-3,6-dioxaoctanoic acid
8-amino-3,6-dioxaoctanoic acid
12-amino-4,7,10-trioxadodecanoic acid 15-amino-4,7,10,13-tetraoxapentadecanoic acid
15-amino-4,7,10,13-tetraoxapentadecanoic acid
18-amino-4,7,10,13,16-pentaoxaoctadecanoic acid
21-amino-4,7,10,13,16,19-hexaoxaheneicosanoic acid
21-amino-4,7,10,13,16,19-hexaoxaheneicosanoic acid
wherein the compound of the invention is formed by a condensation reaction between the succinyl moiety and the amine functionality of the spacer.

In an embodiment, the compound has the structure:

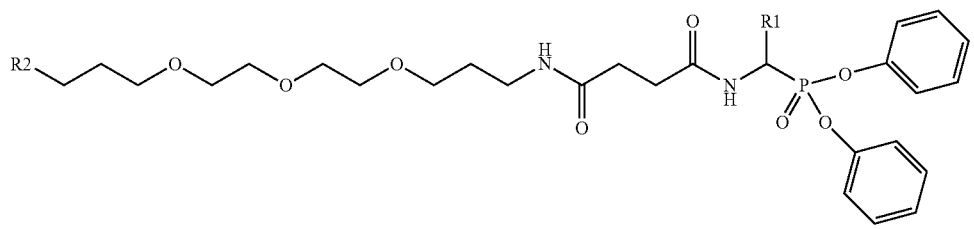

wherein R1 can be H or any suitable amino acid side chain or a derivative thereof, and
wherein R2 can be any suitable reporter group, e.g. biotinyl group or 2,4-dinitrophenyl group, amino acid moiety, peptide group or the like.

In an alternative embodiment, the compound has the structure

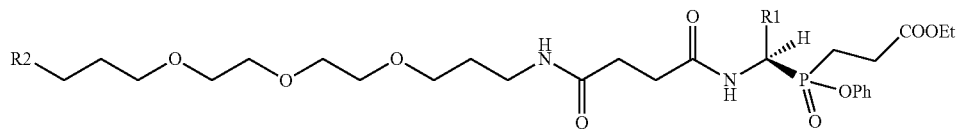

wherein R1 can be H or any suitable amino acid side chain or a derivative thereof, and wherein R2 can be any suitable reporter group, e.g. biotinyl group or 2,4-dinitrophenyl group, amino acid moiety, peptide group or the like.

As will be appreciated suitable derivatives must be capable of providing for the selective binding of the compound of the invention to the biomarker, preferably the protease, for example serine protease of interest. It will be known in the art, what derivatives may be used at such a position instead of or in addition to amino acid residues at R1.

In particularly preferred embodiments, the compound is Biotin-PEG-succinyl moiety-Phe-diphenylphosphonate, Biotin-PEG-succinyl moiety-Val-diphenylphosphonate or Biotin-PEG-succinyl moiety-Lys-diphenylphosphonate.

Advantageously, the compound of the present invention has the following structure:

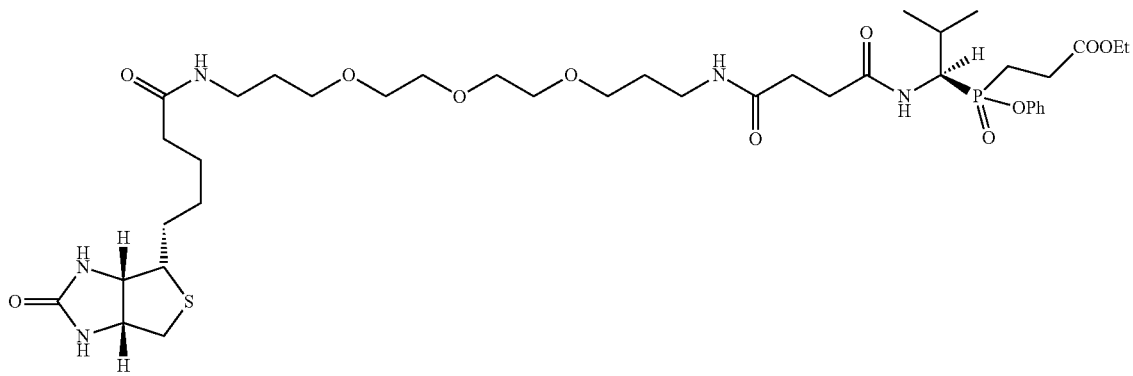

Alternatively, the compound of the present invention may have the structure as shown above wherein the Valyl group is replaced with a Phenylalanyl group, a Lysyl group or an Arginyl group.

According to a second aspect of the present invention, there is provided a method for the detection and/or inhibition of biomarkers in a sample, particularly active proteases, comprising the steps of:

mixing a sample, particularly a biological sample, with a compound of the first aspect of the invention as hereinbefore and hereinafter described, allowing the compound to stably bind a target biomarker in the sample to form a detectable complex, and detecting the detectable complex.

Typically the biomarker is a protease, in particular an active serine protease. Typically the serine protease may be an elastase-like protease, for example neutrophil elastase (NE) or similar, a trypsin-like protease, for example the majority of KLKs, or a chymotrypsin-like protease, for example PSA, KLK-7 and KLK-9 or similar. According to one embodiment, the serine protease may be a neutrophil-derived protease such as neutrophil elastase, cathepsin G, proteinase-3 or similar. Preferably, the serine protease is NE.

Preferably, the sample is a biological sample which may be derived from a cell, tissue, organ, body fluid, fluid derived from body cavity and/or a potentially pathological site, e.g. a site of potential inflammation, malignancy or the like, a lavage fluid or similar.

Typically the body fluid is saliva, blood, lymphal fluid, gingival crevicular fluid, airways fluid, for example induced or expectorated sputum or bronchoalveolar lavage, supernatant from a tissue homogenate or cell preparation, faecal fluid, ascites or wound fluid or the like. Cells or tissue may be appropriately processed to yield a fluid e.g. using a buffer, a cell lysis buffer or the like and maceration, homogenation and/or centrifugation. Lavage fluid may suitably be bronchoalveolar lavage fluid. The lavage fluid may for example be derived from bronchoscopy of CF, COPD, lung cancer, bronchiectasis or other chronic or acute airways disease patient.

The fluid derived from a potentially pathological site may suitably be gingival crevicular fluid from periodontal disease patients. It is particularly preferable to determine neutrophil-derived serine proteases in the crevicular fluid from periodontal disease patients, as these proteases are associated with periodontal disease.

If a fluid and/or tissue is derived from a potentially pathological site, for example a site exhibiting malignancy, kallikrein and/or plasminogen activator are preferably detected.

Additionally, the biological sample e.g. sputum may suitably be processed, for example washed with buffer and vortexed, lysed, homogenised, centrifuged, at least partially fractionated, at least partially purified or the like. Blood may be fractionated to yield either plasma or serum.

The amount of compound to be added depends on the type of biological sample and the biomarker to be detected. Typically, for detection of an active protease 1 to 10 µl of a 10 mM solution of compound is added per ml of an aqueous biological sample; more suitably 5 µl of a 10 mM solution of compound is added per ml of an aqueous biological sample.

The time delay between mixing the sample and the compound and detecting the detectable complex depends upon the amount of sample to be assessed, and the active protease to be detected. Typically the time delay will be 5 minutes to 1 hour suitably less than 30 min.

The method of the present invention thus provides a quick, practical and reliable method of detecting and/or inhibiting target protease biomarkers. This enables the routine detection of proteases, for instance in clinics and hospital laboratories.

According to one embodiment of a method of the invention utilising a compound of the invention, the method for the detection comprises the use of an Enzyme Linked Immuno Sorbent Assay (ELISA). Typically the detectable complex is captured through contact with a substrate comprising a capture group which binds to the detectable complex immobilizing it onto the substrate. Typically the capture group can bind to the reporting group. Suitably in an embodiment the substrate can be coated with a capture group comprising streptavidin, and the reporting group can be biotin. Any suitable substrate may be used such as plate(s), beads, disc, particles, arrays or the like. The complex of the compound of the invention and biomarker wherein the complex is bound to a substrate may be detected by, for instance, immunodetection using a specific antibody-enzyme conjugate to the biomarker, for example the active protease.

In embodiments, the detecting antibody e.g. in the case of an elastase assay would be anti-(species e.g. human neutrophil) elastase and could be either a monoclonal or a polyclonal antibody containing an enzyme conjugate such as horseradish peroxidase (HRP), alkaline phosphatase (AP) or the like. Quantification of the bound, active protease would therefore be through the conversion of a complementary substrate to a readable product eg. Chromogenic substrates such as 3,3',5,5'-tetramethylbenzidine (TMB), 2,2'-Azinobis[3-ethylbenzothiazoline-6-sulfonic acid (ABTS) or o-phenylenediamine dihydrochloride (OPD) for conversion by HRP or in the case of AP, p-Nitrophenyl Phosphate (PNPP); or any suitable chemiluminescent, chemifluorescent or raman substrate for development with HRP.

Alternatively, a specific non-neutralising (i.e. where binding to the biomarker does not interfere with the exposure of the biomarker's active site to the compound) antibody-conjugate to the biomarker may be added to the biological sample before or during mixing with the compound of the present invention. According to one embodiment the antibody and the compound of the present invention are added to the biological sample in a single step. For example, the required reagents are added simultaneously or a premix comprising the required reagents is added. The simultaneous addition of the required reagents would reduce the overall assay time. The simultaneous addition of the required reagents is particularly appropriate where the antibody would not interfere with the active site of the biomarker, in particular where the biomarker is a protease. The simultaneous addition of the required reagents may also be particularly appropriate where the biological sample is in the form of a crude mix such as a cell lysate, partly purified protein mixture or the like.

The complex of the compound of the invention and the biomarker may be immobilized as noted above, and detected accordingly. In general, the same methods of detection may be used regardless of whether the antibody is added to the mixture, before or after addition of the compound of the present invention. Alternatively, the solid support/substrate may be coated with a specific non-neutralising antibody which may be used to immobilize the biomarker onto the solid support. The compound may then be added to the assay after an appropriate wash step to irreversibly bind with the antibody-immobilised biomarker and the complex detected by the addition of an appropriate conjugate. For example, in a case where the reporter group on the compound is biotin then a streptavidin-HRP conjugate is able to bind to the reporter group and the complex quantified through conversion of a suitable HRP substrate as noted above.

In embodiments, the assay can be carried out at room temperature. Alternatively, the assay can be carried out at suitable elevated temperatures, for example 30° C. to 38° C., e.g. approximately 37° C. It will be appreciated that results can be obtained faster if the reaction temperature is at or close to the optimum reaction temperature, generally 30 to 38° C., preferably approximately 37° C.

Preferably, at least one suitable wash step is performed to at least partially purify the biomarker. Typically the wash step is performed after formation, but before detection of the detectable complex. Any suitable washing solution known to the skilled man may be used, such as a wash buffer, for example a phosphate buffered saline or tris-buffered saline, preferably containing 0.05% (v/v) Tween-20.

Depending on the solid support substrate and the mechanism of capture i.e. either by capture antibody or compound the method may include the step of blocking of unbound sites on the solid support, typically before the sample is mixed with the compound. This step may be effected through the addition of a suitable peptide, protein or protein mixture, such as bovine serum albumin, ovalbumin, casein, gelatin, skimmed milk or the like.

Preferably, the step of detecting the detectable complex is performed using at least one suitable substrate, preferably an aqueous substrate, capable of conversion to a detectable product, in particular a differently coloured product. According to one embodiment the substrate is 3,3',5,5'-Tetramethylbenzidine (TMB) or p-nitrophenyl phosphate. The substrate can be converted by either horseradish peroxidase or alkaline phosphatase conjugated to either streptavidin or a specific antibody.

Additionally or alternatively, suitable fluorogenic, luminescent or raman substrates can be used. As will be appreciated, such substrates can increase detection sensitivity down to nano and picogram levels.

The method has the advantage that it is highly specific, as the specific recognition group of the compound is recognised by a specific recognition sequence of the target biomarker. Furthermore, the method provides good detection sensitivity as the compound has a high affinity to the target biomarker.

Where the method of detection is performed on a control sample, at least 90 percent of the biomarker present is detected. Suitably 95 to 100 percent of the biomarker present is detected; advantageously approximately 99 percent of the biomarker present is detected.

According to one embodiment the method may be used to detect more than one biomarker in a sample through the use of more than one compound of the present invention, where each compound of the present invention added to the sample has a different affinity. Typically more than one protease is detected in a sample. Each compound of the present invention may be added to the sample simultaneously or sequentially.

According to a third aspect of the present invention, there is provided a compound as hereinbefore and hereinafter described for use in the detection and/or inhibition of biomarkers, particularly active serine proteases.

According to a fourth aspect of the present invention, there is provided a method of detecting or monitoring of a pathological condition in a subject comprising the steps of:
providing a sample from the subject,
incubating the sample with a compound as hereinbefore and hereinafter described for binding biomarker, in particular an active target serine protease, in order to form a detectable complex and determining the amount of biomarker in the sample through,
analysis of the amount of the detectable complex present,
comparing the amount of biomarker in the sample with a normal level of protease in such a sample, and
wherein an elevated level of the biomarker compared to a normal level is indicative of a pathological condition.

Typically the biomarker is a protease, in particular an active serine protease. Typically the serine protease may be an elastase-like protease, for example neutrophil elastase (NE) or similar, a trypsin-like protease, for example the majority of KLKs, or a chymotrypsin-like protease, for example PSA, KLK-7 and KLK-9 or similar. According to one embodiment, the serine protease may be a neutrophil-derived protease such as neutrophil elastase, cathepsin G, proteinase-3 or similar. Preferably, the serine protease is NE.

The percentage increase of biomarker is dependent on the target protease, as well as on the nature of the pathological condition. Typically the amount of active protease is increased by at least 10-fold compared to the normal level, and can exceed 100-fold depending on the disease and health status of the patient. Typically active proteases are not detected in healthy individuals, at such elevated levels. For instance, active proteases are generally not detected in the lungs of healthy individuals.

The normal level of biomarker may be a range, in which case the amount of biomarker in the sample is compared to the upper range of the normal range.

Where the biomarker is a protease, an increase of 5-fold or more is generally indicative of a pathological condition. Typically pathological conditions may be associated with an increase of up to 100-fold or more.

According to one embodiment, the pathological condition is inflammation, including airways diseases such as cystic fibrosis (Mayer-Hamblett et al., 2007) chronic obstructive pulmonary disease (Djekic et al., 2009), bronchiectasis, emphysema, congenital alpha1-antitrypsin deficiency and acute respiratory distress (ARDS) (Hayakawa et al., 2010); atherosclerosis (Henriksen and Sallenave, 2008), pancreatitis (Frossard et al., 2001); acute periodontal disease (Özçaka et al., 2010); solid malignancies (Sato et al., 2006) and haematological malignancies e.g. leukaemias; disseminated intravascular coagulation, sepsis (Hayakawa et al., 2010), aneurysms (Gaetani et al., 1998), chronic non-healing wounds (Trengove et al., 1996), bacterial, viral or fungal infection or the like. As discussed herein, it would be advantageous to provide a rapid method of detecting active proteases, as the determination of active proteases can be useful in diagnostic and/or prognostic tests. It may be useful to detect a broad set of active proteases or one or more of a particular protease, for example selected from Elastase, chymotrypsin-like or trypsin-like protease; metalloproteinases, such as gelatinases, matrilysin or intestinal collagen; cysteine, for example cathepisn, B, L, S or caspases.

Using the linked reporter group (reporter group and spacer)-specific recognition sequence and binding group (capture ligand (warhead)) compounds of the present invention, the inventors have developed assay test kits to specifically and selectively detect proteases from test samples.

The assay test kits may utilise ELISA to quantify the level of protease in a sample, lateral flow device such as dipstick technology or protease chip technology.

Assay kits may suitably be used to investigate either diagnostically or prognostically diseases or conditions such as, for example, respiratory diseases (cystic fibrosis, bronchiectasis and COPD), cancer, leukaemia, cardiovascular disease and bacterial infection.

Additionally, the kits may be used in drug discovery to screen libraries of compounds for the identification of specific inhibitors, which could be used for example as antiprotease therapies in a range of pathological disorders. Accordingly, such drug screening assays wherein a test compound and a compound of the present invention are provided to a protease and the inhibition of the binding of the compound of the invention to the protease in relation to the presence of a test compound can be a further aspect of the present invention.

Advantageously, the kit of the present invention measures active proteases, not proteases which have already been inactivated through neutralisation with an endogenous inhibitor and are therefore no longer capable of causing tissue damage, propagating inflammation or activating other biochemical entities. For example, NE is inactivated in a 1:1 stoichiometric manner by its native inhibitor alpha$_1$-antitrypsin. Once bound it is subjected to degradation and no longer clinically relevant. Measurement of this protein would therefore not be useful for either diagnosis or prognosis. Standard antibody-only ELISA's detect total biomarker protein which in the case of NE would encompass both active free NE and inactive complexed NE/AAT.

According to a fifth aspect of the present invention, there is provided an assay system or kit for detection of a biomarker, comprising a compound as hereinbefore and hereinafter described.

Particularly, the biomarker is an active serine protease, for example an elastase-like, trypsin-like and chymotrypsin-like protease. As will be appreciated, the assay system comprising such compound provides high specificity and sensitivity, is fast and user-friendly. Further, the assay system is easy to use and has a high predictive value.

In one embodiment, the assay system may be in the form of an ELISA assay, lateral flow device including dipstick, chip, or the like.

In a preferred embodiment, the method for the detection is an ELISA (Enzyme Linked Immuno Sorbent Assay). The ELISA can include selective capture of a complex formed from the biomarker and the compound of the present invention using a substrate comprising a capture group such as streptavidin. Suitably the substrate can be in the form of a streptavidin coated plate(s), bead(s) or the like. Following capture of the complex on the substrate the complex can be detected, for example by immunodetection using a specific antibody to the biomarker or the like. Alternatively, immunocapture using a specific antibody to the biomarker can also be used to selectively target and/or isolate the biomarker in a crude mix, such as a cell lysate, partly purified protein mixture or the like, prior to the addition of the compound for subsequent detection. In this case subsequent detection can be performed by the formation of a biotin-streptavidin-peroxidase conjugate formed from the complex of the compound and the capture biomarker. This may be performed as a single step reaction. For example, use of an antibody which does not interfere with the active site of the biomarker may allow the simultaneous provision of antibody and the compound of the present invention to a sample. For example, in a particular assay system format the required reagents can be added simultaneously or a premix comprising the required reagents is added, thus reducing the overall assay time.

The ELISA format is advantageous, since it provides a quantitative format, which is labour and time friendly, typically 3.5 hr and normally no more than 4 hrs.

In particular, the ELISA format is advantageous for assaying active NE, which can be captured by a compound being specific for NE. A subsequently applied specific antibody-conjugate provides additional signal amplification, thereby providing much greater sensitivity.

Incubation with the antibody will generally take 5 min to 2 hours, particularly approximately 1 hour. This short term incubation is particularly advantageous, as results can be quickly obtained.

As will be appreciated, the lateral flow device or dipstick assay format is advantageous as it is robust, convenient and easy to use. Furthermore, it may easily be incorporated into the routine assessment of patients either at point of care or for personal monitoring as an at-home test kit. It will be appreciated that the lateral flow device/dipstick assay format is particularly useful in the clinic for a qualitative and possibly semi-quantitative result which could aid patient monitoring and provide an early marker which could inform clinical decisions regarding treatment, including prophylactic treatments.

According to a sixth aspect of the present invention, there is provided a kit for detecting a biomarker, particularly an active serine protease, comprising a compound as hereinbefore and hereinafter described.

According to one embodiment the kit further comprises at least one suitable detection agent, which is capable of detecting, e.g. binding to, a reporter group of the compound as hereinbefore and hereinafter described.

Preferably, the kit comprises a suitable support, e.g. a solid matrix support. The matrix support may be a membrane such as nitrocellulose, a resin, such as N-MCA-N$^1$-FMOC-ethylene-diamine MPB-AM resin (typically sold under the trade name NovaTag™) or the like. Preferably, the at least one binding agent can be at least temporarily bound to the support. For example, the binding agent is covalently bound to the support. Additionally, further assay components can be bound, e.g. covalently bound, to the support.

In alternative embodiments, the kit comprises a suitable detection device, which is capable of detecting a suitable reporter group of the compound, e.g. a dye, fluorogenic substrate or the like. For example, the detection device comprises a light source (UV or vis), fluorescence, luminescence, a laser or the like.

Preferably, the kit comprises at least one suitable buffer component, e.g. a buffer premix, buffer solution or the like. As will be appreciated, the buffer component assists with sample preparation.

It may be of assistance to a user of the kit if the kit comprises a reference such as a colour card giving the range of the assay for guidance of acceptable or unacceptable clinical levels or the like.

According to a seventh aspect of the present invention, there is provided a product or device for specifically detecting active serine proteases, comprising a compound as hereinbefore and hereinafter described and a matrix to which the compound is permanently or semi-permanently attached, e.g. bound.

Particularly, the product may be a lateral flow device such as a dipstick, chip, membrane, plate or the like. In embodiments the product can comprise an absorbent pad, a test membrane, an immobilised antibody and a compound of the present invention wherein the absorbent pad is arranged to receive a test sample such that the test sample is brought into contact with a compound of the present invention such that if a protease being tested is present in the sample it can form a complex with the compound. The complex can then migrate through the device and bind to a conjugate with a detecting agent for example streptavidin-colloidal gold. The expanded complex can then migrate through the device, for example typically by lateral flow. The expanded complex can then be bound by the immobilised antibody, for example immobilised antibody specific to the protease under investigation. Preferably binding of the complex by the immobilised antibody can be visualised in a test window. In preferred embodiments the product can further comprise an immobilised antibody with binding specificity to the reporter group of the compound or detecting agent of the conjugate.

In embodiments at least two compounds may be provided wherein at least two compounds have specificity to different proteases, for example a first compound with specificity to elastase and a second compound with specificity to chymotrypsin or trypsin like proteases.

According to an eighth aspect of the present invention, there is provided a method of identifying a compound capable of specifically binding a target biomarker, in particular an active serine protease, for use in an assay system, comprising the steps of:

provicing a compound, said compound comprising,
a binding group capable of stably binding the target biomarker,
a specific recognition group, particularly a peptidyl group, for the target biomarker,
a spacer group, and
a reporter group, which is connected with the recognition group by the spacer group, and preferably a succinyl moiety between the spacer group and the specific recognition group,
incubating the compound with the target biomarker and at least one other biomarker, in particular at least one other active serine protease and
determining whether a detectable complex has formed with the target biomarker only,
wherein a detectable complex with the target biomarker only is indicative of the compound being capable of selectively binding the target biomarker.

Suitably in the method there is provided a compound of the present invention as herein described.

This is particularly advantageous, as a variety of specific compounds or families of specific compounds can conveniently and rapidly be developed for use in an assay system, such as ELISA assay format, lateral flow device/dipstick assay format, chip format or the like.

In embodiments of the invention, an assay system or kit comprising a compound of the invention can be a lateral flow device or dipstick. Such embodiments may suitably be formed for use in a point of care assay to assist with patient management or as a home testing kit for personal disease management and monitoring.

Figure 2:
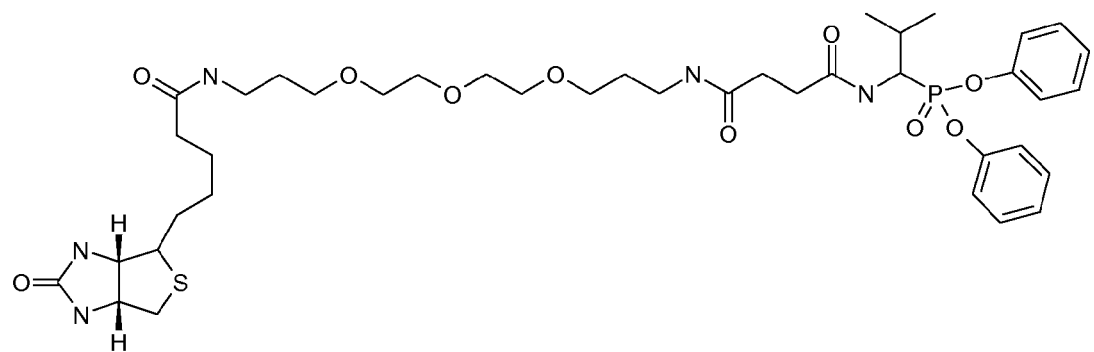
Figure 3:
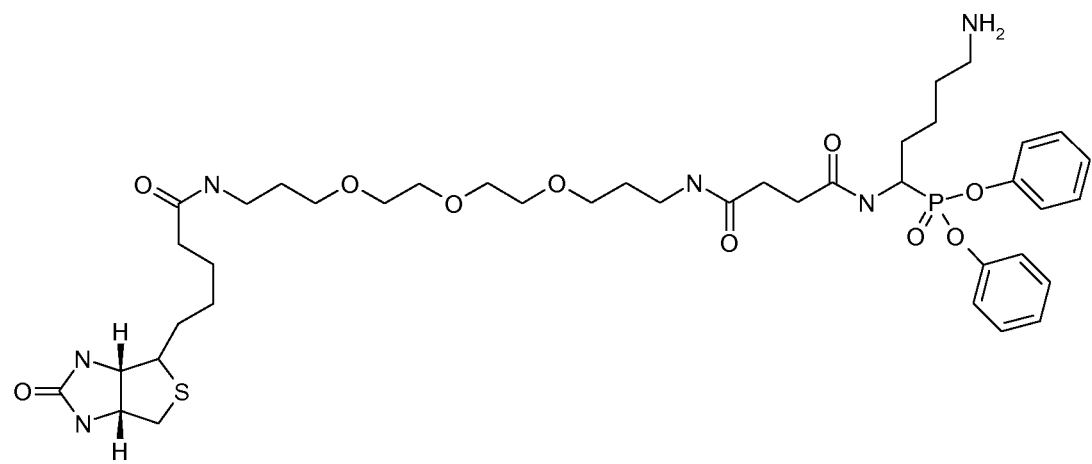
Figure 4:
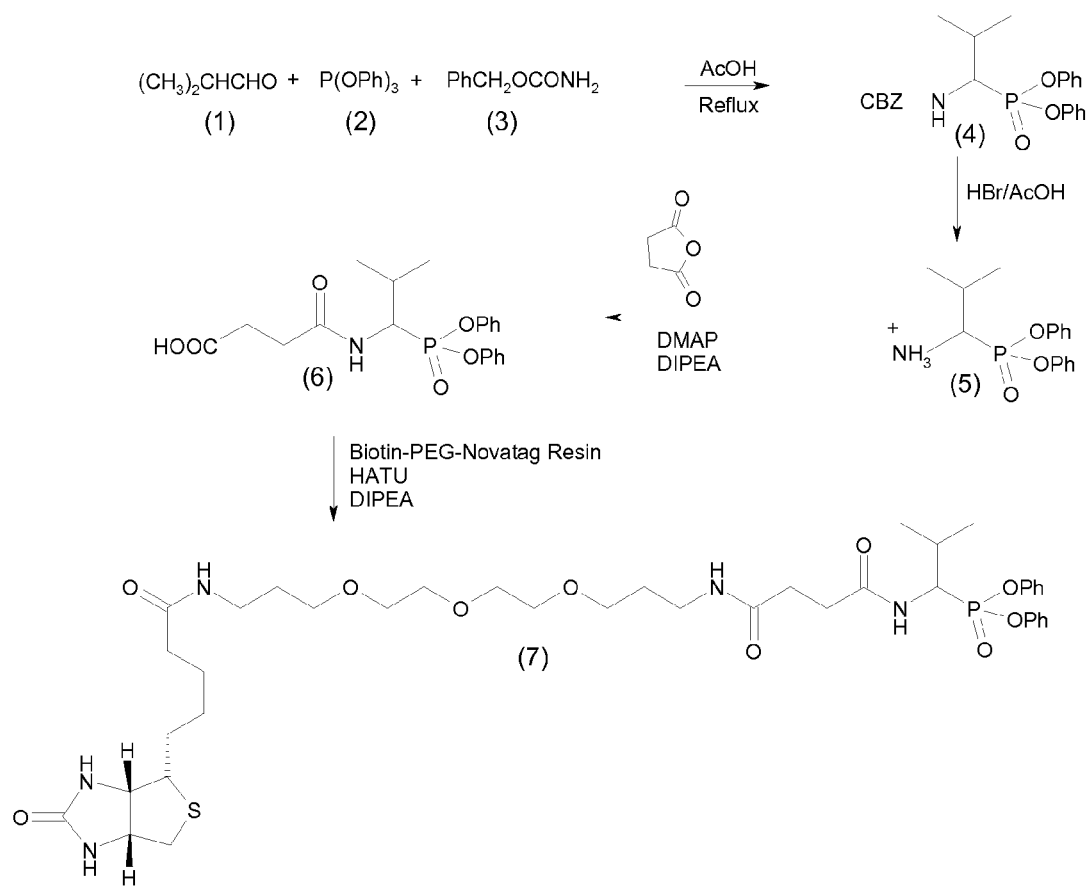
Figure 5:
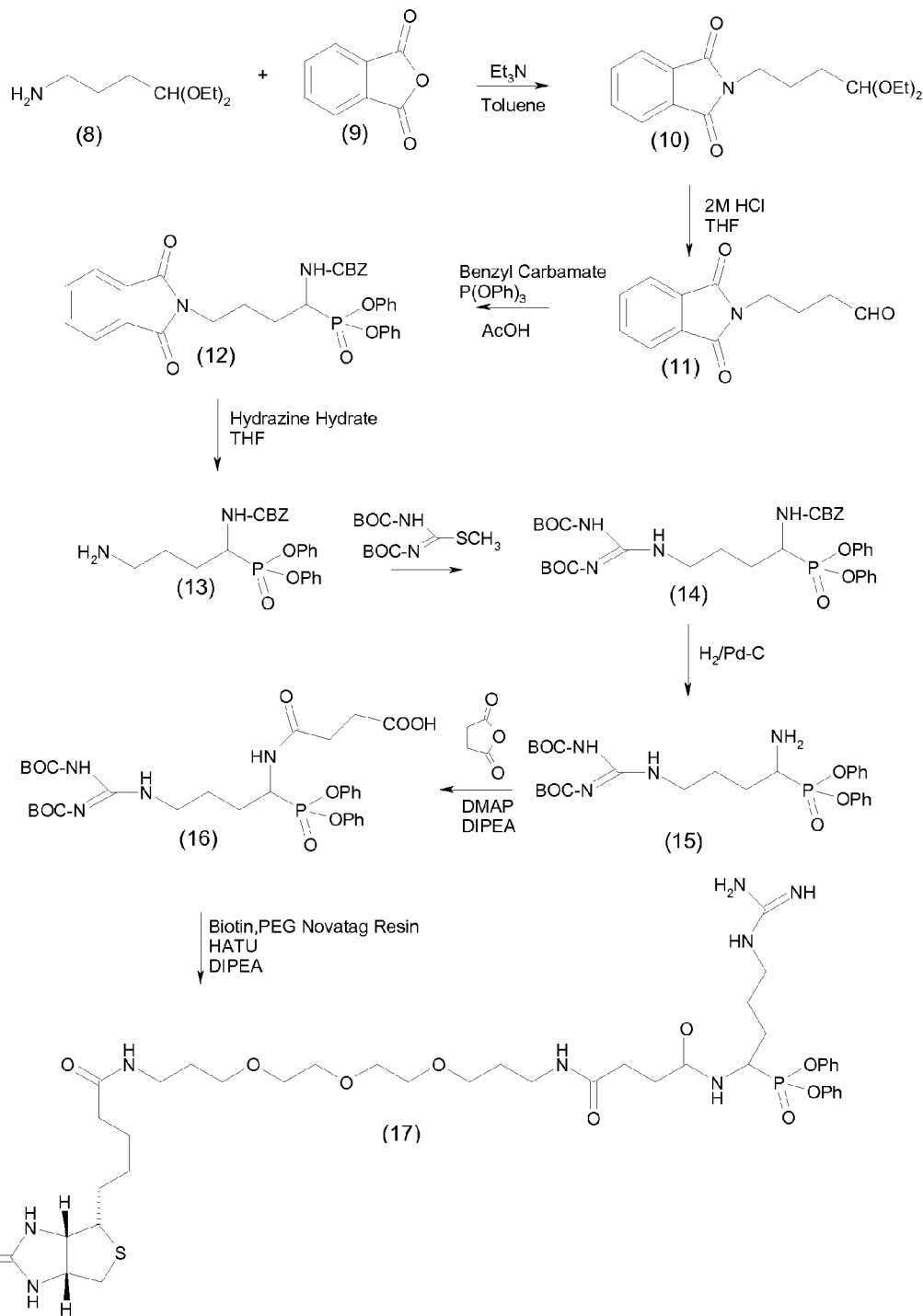
Figure 6:
Figure 7:
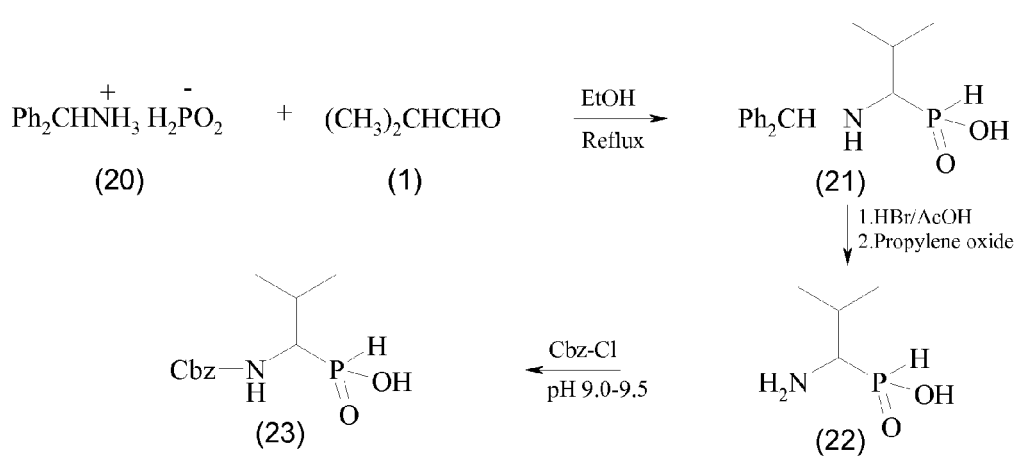
Figure 8:
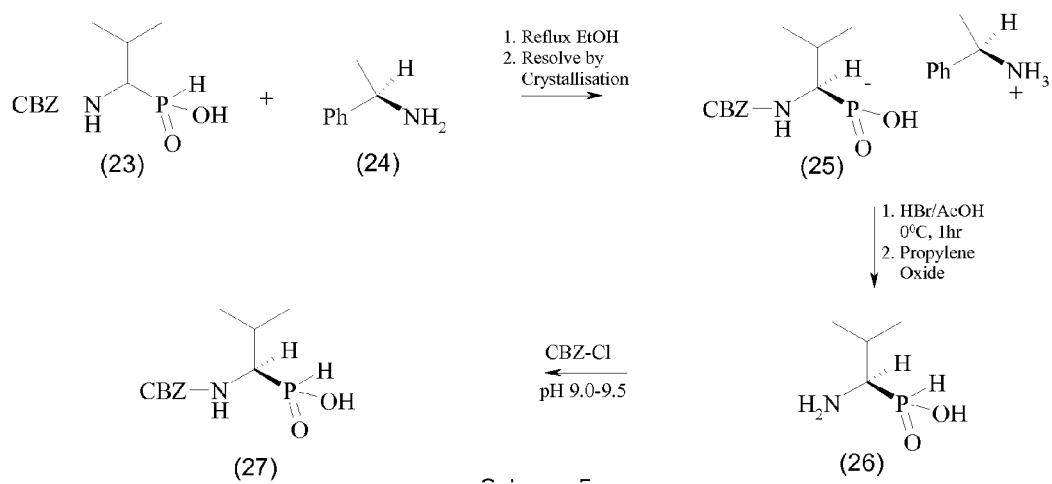
Figure 9:
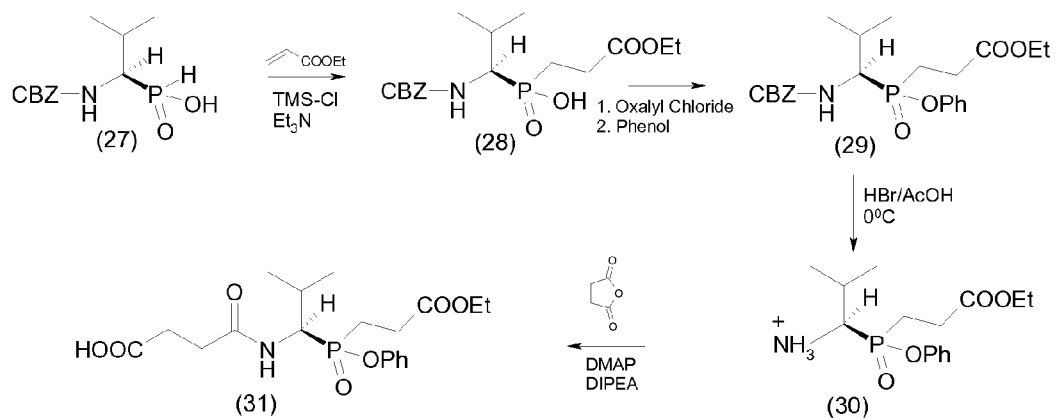
Figure 10:
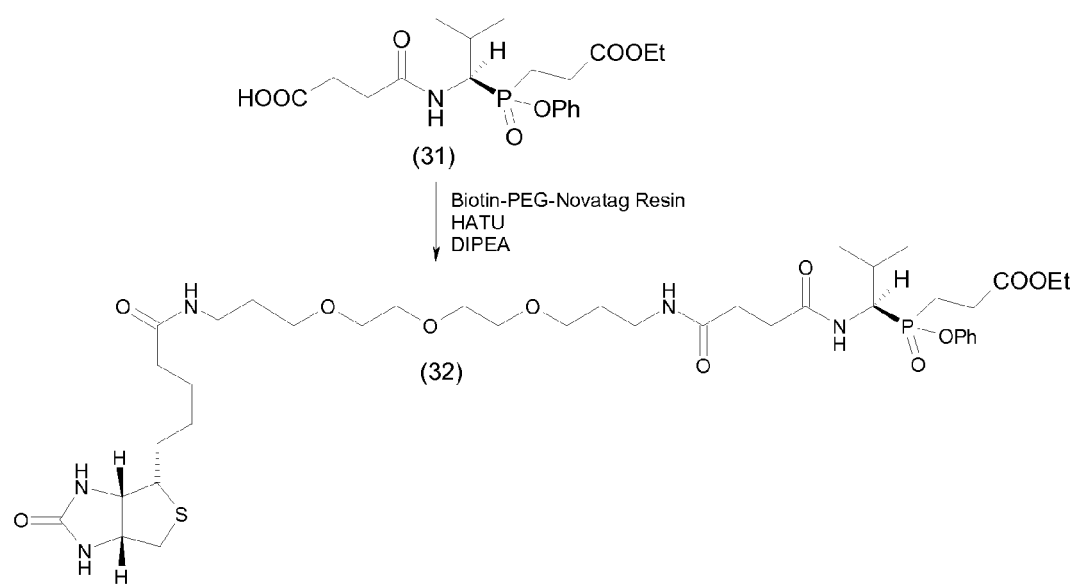
Figure 11:
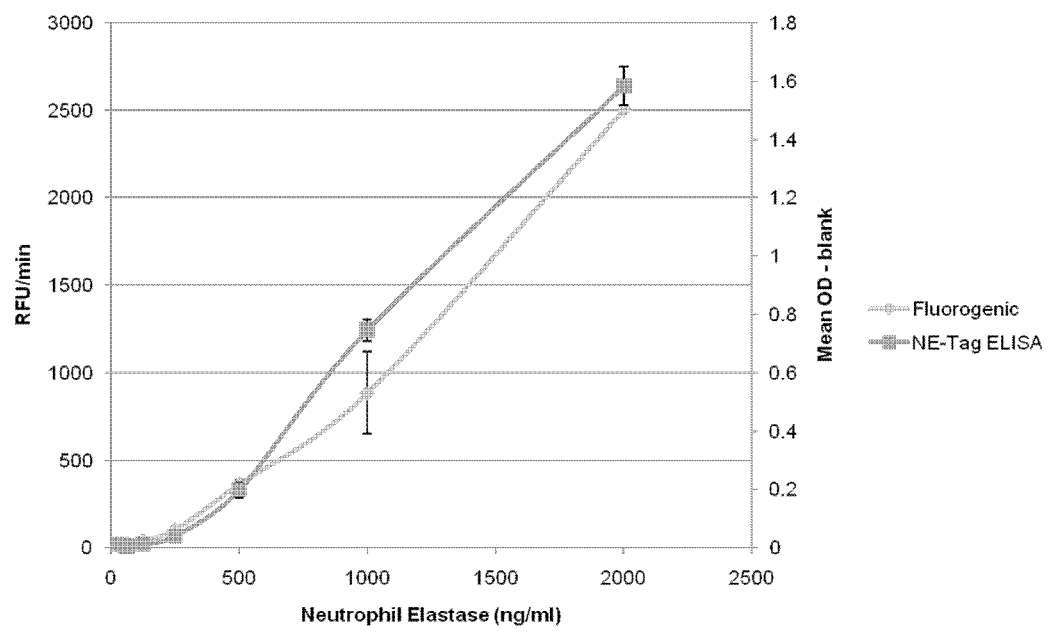

The invention will now be described further in the following non-limiting examples with reference to the accompanying drawings in which:

FIG. 1 shows a schematic representation of a Biotin-PEG-Phe-diphenylphosphonate, FIG. 2 shows a schematic representation of a Biotin-PEG-Val-diphenylphosphonate, FIG. 3 shows a schematic representation of a Biotin-PEG-Lys-diphenylphosphonate, FIG. 4 shows a schematic representation of the synthesis of Biotin-PEG-Succ-Val$^P$(OPh)$_2$, FIG. 5 shows a schematic representation of the synthesis of Biotin-PEG-Succ-Arg$^P$(OPh)$_2$, FIG. 6 shows a schematic representation of the preparation of phosphonous acid salt, FIG. 7 shows a schematic representation of the synthesis of racemic Valine analogue, FIG. 8 shows a schematic representation of the synthesis of (R)-Cbz-Val$^P$(OH)H, FIG. 9 shows a schematic representation of the synthesis of (R)-Succ. Val$^P$ analogue, and FIG. 10 shows a schematic representation of the coupling of (R)-Succ-Val$^P$ Analogue to Biotin-PEG-NovaTag™ Resin FIG. 11 illustrates NE-Tag ELISA vs fluorescence activity assay wherein the Y axis is RFU/min and X axis is Neutrophil elastase (ng/ml) ■ shows NE-Tag ELISA using compound of the invention and ♦ shows fluorogenic activity assay, and FIG. 12 shows results of comparative assays wherein data is presented as Spearman's rho (p value), ** Correlation significant at 0.01 level (2-tailed), * Correlation significant at the 0.05 level (2-tailed), ND. Not done due to insufficient sample, and FIG. 13 shows correlations of NE with clinical data wherein statistical data are presented as Pearson r value (p value), † Non-parametric data is presented as Spearman's rho (p value), ** Correlation significant at 0.01 level (2-tailed), * Correlation significant at the 0.05 level (2-tailed).

In FIG. 1 a schematic representation of Biotin-PEG-Phe-diphenylphosphonate is shown. Biotin-PEG-Phe-diphenylphosphonate has the molecular formula $C_{44}H_{60}N_5O_{10}PS$ and a molecular composition of 59.92% C, 6.86% H, 7.94% N, 18.14% O, 3.51% P and 3.64% S. It has a molecular weight of 882.03 and a mass of 881.

In FIG. 2 a schematic representation of Biotin-PEG-Val-diphenylphosphonate is shown. Biotin-PEG-Val-diphenylphosphonate has the molecular formula $C_{40}H_{60}N_5O_{10}PS$ and a molecular composition of 57.61% C, 7.25% H, 8.40% N, 19.18% O, 3.71% P and 3.84% S. It has a molecular weight of 833.99 and a mass of 833.

In FIG. 3 a schematic representation of Biotin-PEG-Lys-diphenylphosphonate is shown. Biotin-PEG-Lys-diphenylphosphonate has the molecular formula $C_{41}H_{63}N_6O_{10}PS$ and a molecular composition of 57.06% C, 7.36% H, 9.74% N, 18.54% O, 3.59% P and 3.72% S. It has a molecular weight of 863.03 and a mass of 862.

EXAMPLE I

Synthesis of Biotin-PEG-Succ-Val$^P$(OPh)$_2$

Biotin-PEG-Succ-Val$^P$(OPh)$_2$ was synthesized according to the scheme as shown in FIG. 4.

Isobutyraldehyde (1), triphenylphosphite (2) and benzylcarbamate (3) were heated in acetic acid to provide Cbz-Val$^P$(OPh)$_2$ (4) which was deprotected using 33% v/v HBr/AcOH (typically incubated at room temperature for 90 minutes). The resulting HBr salt (5) was reacted with succinic anhydride and the succinyl derivative formed (6) coupled to Biotin-PEG-Novatae Resin using HATU/DIPEA to give (7) as shown in FIG. 4.

EXAMPLE II

Synthesis of Biotin-PEG-Succ-Arg$^P$ (OPh)$_2$

Biotin-PEG-Succ-Arg$^P$ (OPh)$_2$ was synthesized according to the scheme as shown in FIG. 5.

4-(N-phthaloyl)butyraldehyde (10), (prepared from phthalic anhydride (9) and 4-aminobutyraldehyde diethylacetal (8)) was heated with triphenyl phosphite and benzyl carbamate in AcOH to give N-ω-Pth-N-α-Cbz-Orn$^P$(OPh)$_2$ (12). Removal of the phthaloyl group using hydrazine hydrate followed by reaction with N,N'-bis-Boc-S-methylthiourea yielded the arginine derivative (14) which was deprotected at the α-N by catalytic hydrogenolysis using H$_2$-10% Pd/C. The deprotected material (15) was then reacted with succinic anhydride and coupled to Biotin-PEG-Novatag Resin using HATU/DIPEA to give (17).

EXAMPLE III

Synthesis of Biotin-PEG-Succ-(R)-Val$^P$ (CH$_2$CH$_2$CO$_2$Et)(OPh)

(a) Preparation of Phosphonous Acid Salt

Phosphonous acid salt was synthesized according to the scheme as shown in FIG. 6.

Anhydrous hypophosphorus acid (19), (prepared from 50% W/V aqueous solution by removal of water under high vacuum at room temperature) and diphenylmethylamine (18) were reacted in anhydrous ethanol and the resulting precipitated product collected by filtration.

(b) Preparation of Racemic Valine Analogue

Racemic Valine analogue was synthesized according to the scheme as shown in FIG. 7.

The hypophosphorus acid-diphenylmethylamine salt (20) and isobutyraldehyde were heated in refluxing ethanol to form the diphenylmethylaminophosphonous acid (21). This was deprotected using 48% hydrobromic acid. Following treatment with propylene oxide the Cbz-protected material (23) was obtained by reacting (22) with benzylchloroformate at pH 9.0-9.5.

(c) Preparation of (R)-Cbz-Val$^P$(OH)H (R)-Cbz-Val$^P$(OH)H was synthesized according to the scheme as shown in FIG. 8.

Racemic Cbz-Val$^P$(OH)H (23) was reacted with (R)-(+)-α-methylbenzylamine (24) in anhyd. ethanol at reflux. The precipitated salt was recovered and recrystallised from anhyd. ethanol several times until the optically pure material [optical rotation ($[α]_D$=−16.40 c, 1 in ethanol)] was obtained. The resolved salt (25) was stirred in 33% HBr/AcOH at 0° C. followed by treatment with propylene oxide to give the (R) amino-phosphonous acid (26) which was reconverted to the Cbz-protected material (27) by reaction with benzylchloroformate at pH 9.0-9.5.

(d) Preparation of (R)-Succ. Val$^P$ Analogue (R)-Succ. Val$^P$ Analogue was synthesized according to the scheme as shown in FIG. 9.

The N-succ-(R)-Val$^P$(CH$_2$CH$_2$CO$_2$Et)(OPh) analogue (31) was prepared from (R)—N-Cbz-phosphonous acid (27) by reaction with ethyl acrylate to give phosphinic acid (28) followed by treatment with oxalyl chloride to form the acid chloride and phenol to form the phenyl ester (29). Removal of the Cbz-group with 33% HBr/AcOH and reaction with succinic anhydride gave the required succinyl product (31).

(e) Coupling of (R)-Succ-Val$^P$ Analogue to Biotin-PEG-Novatag Resin (R)-Succ-Val$^P$ Analogue was coupled to Biotin-PEG-Novatag Resin according to the scheme as shown in FIG. 10.

This step was performed under the previously used coupling conditions i.e. HATU/DIPEA, as indicated in examples I and II.

EXAMPLE IV

Binding the Compound Provided by One of Examples I to III and a Target Protease

The compound rapidly binds the target protease at room temperature. However, a temperature of 37° C. is preferred. Binding is achieved by adding the compound at a suitable (or the optimal concentration) typically to give a final concentration of 10 μM to a sample comprising the target protease and incubating it for approximately 15 minutes or another suitable time in order to form a complex. The complex can either be detected using ELISA as described above; by sodium dodecyl sulphate polyacylamide gel electrophoresis (SDS-PAGE) followed by electroblotting onto nitrocellulose and detection using a suitable agent, e.g. steptavidin or a relevant antibody, conjugated to an enzyme such as alkaline phosphatase or preferably horseradish peroxidase; by dot-blotting or by a lateral flow device such as a dip-stick assay.

EXAMPLE V

An assay kit can comprise a pre-coated streptavidin substrate, for example, a commercially available streptavidin plate, and a compound of the present invention is provided. Optionally, the kit can further include an antibody or binding member with binding specificity to the protease to which the compound has binding specificity with a reporter conjugated thereto.

In an embodiment, an assay kit can comprise a pre-coated streptavidin plate, which is able to bind to a compound of the present invention with binding specificity to neutrophil elastase and a biotin linked reporter group.

The test sample can be mixed with the compound of the invention and applied to the pre-coated streptavidin plate such that the biotin linked reporter group of the compound of the invention can bind to the streptavidin on the plate. Incubation times of the sample to the plate may be optimised for suitable binding to occur. The plate can then be washed with buffer and an anti-neutrophil elastase-peroxidase conjugate antibody used to probe the washed plate. As the plate will retain active neutrophil elastase which had been bound by the compound of the invention the anti-neutrophil elastase-peroxidase conjugate antibody will bind to the retained neutrophil elastase only and the peroxidase can be used to perform an ELISA reaction to determine the level of neutrophil elastase present. Optionally, a blocking buffers can be included in the kit and the method can include a step of adding the blocking buffers to minimise the likelihood of non-specific binding by the anti-protease conjugate antibody to the plate.

FIG. 11 illustrates such an NE-Tag ELISA test and a fluorescence activity assay, The NE-Tag Test had a detection range of around 250-3500 ng/ml and was sensitive to about 125 ng.

EXAMPLE VI

Comparison of Three Test Systems

Sputum samples were collected from randomly selected subjects hospitalised for acute exacerbation of cystic fibrosis.

The samples were split such that a fraction of samples were centrifuged at 30,000 g for 1 hour at 4° C., while another fraction was diluted 4 parts PBS (phosphate buffered saline), and mechanically rotated for 1 min before centrifugation at 3000 g for 30 min at 4° C.

NE Activity was then detected using a conventional Fluorescence activity test, using Innozyme™ NE conventional immunocapture activity assay (Calbiochem) and the ELISA test discussed in Example V. The results of these tests are provided at FIGS. 11 and 12.

Advantageously, the NE-TAG ELISA test provided for selective capture coupled with specific immunodetection and correlated appropriately with clinical parameters.

EXAMPLE VII

An assay kit to detect protease utilising compounds of the invention can also be provided as a lateral flow device/dipstick test.

In such an embodiment a dipstick can comprise, a compound of the invention which can specifically bind to a protease of interest, a sample receiving portion, an immobilised antibody with binding specificity to the protease of interest, a test result portion and optionally a control portion.

The sample to be tested is provided to the sample receiving portion, for example an absorbent pad in communication with a test membrane. The compound of the invention is permitted to form a complex with protease in the test sample to which the compound of the invention has binding specificity, for example a compound of the invention with binding specificity to NE can bind to active NE present in the test sample.

The protease bound to the compound of the invention with a suitable linked reporting group can then be brought into communication with the immobilised antibody, for example utilising a fluid path on a test membrane on which an antibody can be immobilised, such that the complex can be concentrated by the immobilised antibody at a test result portion, for example a viewing window where the reporter portion of the compound of the invention can be detected.

Optionally, the dipstick may further comprise a control portion which, for example comprises immobilised antibodies with binding specificity to the reporter of the compound of interest, located past the flow path of the immobilised antibodies with binding specificity to the protease such that it is clear when the sample and compound of interest should have moved past the test result portion.

Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

1. Mayer-Hamblett, N, Aitken, M L, Accurso, F J, Kronmal, R A, Konstan, M W, Burns, J L, Sagel, S D and Ramsey, B W (2007) *Am. J. Respir. Crit. Care Med.* 175: 822-828.
2. Fujimoto K, Yasuo, M, Urushibata, K, Hanaoka, M, Koizumi, T and Kubo, K (2005) *Eur. Respir. J.* 25(4): 640-646.
3. Tsang, K W, Chan, K, Ho, P, Zheng, L, Ooi, G C, Ho, J C M and Lam, W (2000) *Chest* 117: 420-426.
4. Loos, B G and Tjoa, S (2005) *Periodontology* 2000 39: 53-72.
5. Paliouras, M. et al. (2007) *Cancer Letts.* 249: 61-79.
6. Hamilton, R, Walker, B J and Walker, B (1993) *Tetrahedron Lett.* 34: 2847-2850
7. Kay, G, Kennedy, R, Walker, B and Nelson, J (1993) *Biochem. Soc. Trans.* 22: 20S
8. Hawthorne, S J, Halton, D W and Walker, B (1994) *Parasitology* 108: 595-601.
9. Hamilton, R, Walker, B and Walker, B J (1998) *Bioorg. Med. Chem. Letts.* 8: 1655-1660.
10. Hawthorne, S, Hamilton, R, Walker, B J & Walker, B (2004) *Anal. Biochem.* 326: 273-275.
11. Walker, B, Wharry, S., Hamilton, R J, Martin, S L, Healy, A, and Walker, B (2000) *Biochem. Biophys. Res. Comms* 276: 1235-1239.
12. Eley, B M and Cox, S W (1998) *Br. Dent. J.* 184: 373-376.
13. Cox, S W, Cho, K, Eley, B M and Smith, R E (1990) *J. Periodont. Res.* 25: 164-171.
14. Pan Z, Jeffery D A, Chehade K, Beltman J, Clark J M, Grothaus, P, Bogyo, M. and Baruch, A. (2006) *Bioorg. Med. Chem. Letts.* 16: 2882-2885.
15. Djekic U V, Gaggar A, and Weathington N M. (2009) *Pharmacol Ther.* 121(2): 132-46.
16. Hayakawa M, Katabami K, Wada T, Sugano M, Hoshino H, Sawamura A, and Gando S. (2010) *Shock* 33: 14-18.
17. Henriksen P A and Sallenave J M. (2008) *Int. J. Biochem. Cell. Biol.* 40(6-7): 1095-100.
18. Frossard J-L, Hadengue, A, and Pastor C M. (2001) *Am. J. Respir. Crit. Care Med.* 164: 162-170
19. Özçaka Ö, Biçakci N, Pussinen P, Sorsa T, Köse T and Buduneli N. (2010) *Oral Diseases.*
20. Sato T, Takahashi S, Mizumoto T, Harao M, Akizuki M, Takasugi M, Fukutomi T, Yamashita J. (2006) *Surg. Oncol.* 15(4): 217-22.
21. Gaetani-P, Tartara F, Grazioli V, Tancioni F, Infuso L and Rodriguez y Baena R. (1998) *Life Sciences* 63: 285-292.
22. Trengove N J, Stacey M C, Macauley S, Bennett N, Gibson J, Burslem F, Murphy G and Schultz G. (1999) *Wound Repair and Regeneration* 7: 442-452.
23. Oleksyszyn, J and Powers, J C (1991) *Biochemistry* 30: 485-493.
24. Oleksyszyn, J and Powers J C (1994) *Methods Enzymol.* 244: 423-441
25. Hamilton, R, Walker, B J and Walker B (1993) *Tet. Letts.* 34: 2847-2850.
26. Hamilton, R, Shute, R E, Travers, J, Walker, B and Walker, B J (1994) *Tet. Letts.* 35: 3597-3600.
27. Hamilton, R, Walker B and Walker, B J (1995) *Tet. Letts.* 36: 4451-4454.

The invention claimed is:

1. A compound, for detection of a specific protease in a sample, wherein the compound comprises:

a binding group capable of stably binding the protease, said binding group comprising a monophenylphosphinate group or a diphenylphosphonate group, a specific recognition group for the protease, which is an amino acid group(s) positioned at P1 and/or P2 or P1, P2 and P3, a succinyl moiety, a spacer group comprising one or more PEG residues, and a reporter group wherein the binding group is linked to the specific recognition group, the specific recognition group is linked to the succinyl moiety, the succinyl moiety is linked to the spacer group and the spacer group is linked to the reporter group and wherein the compound is:

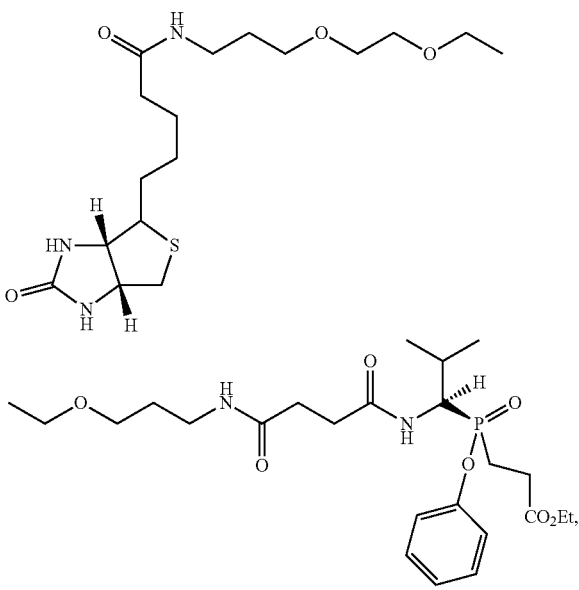

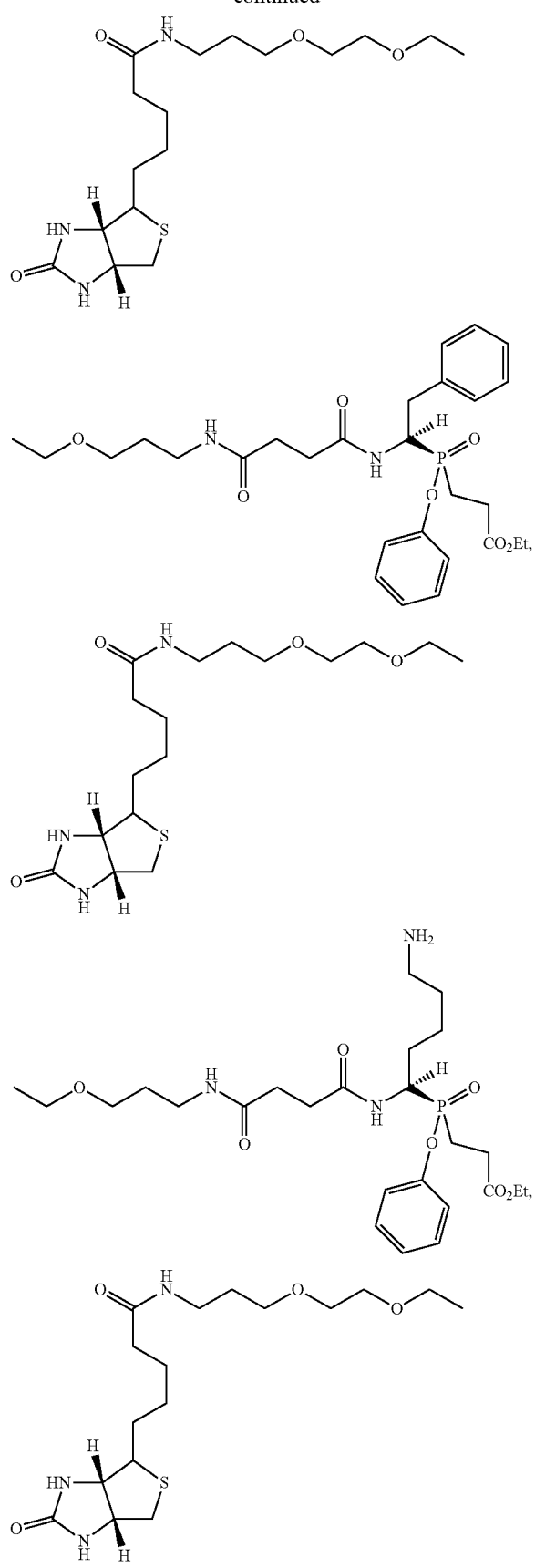
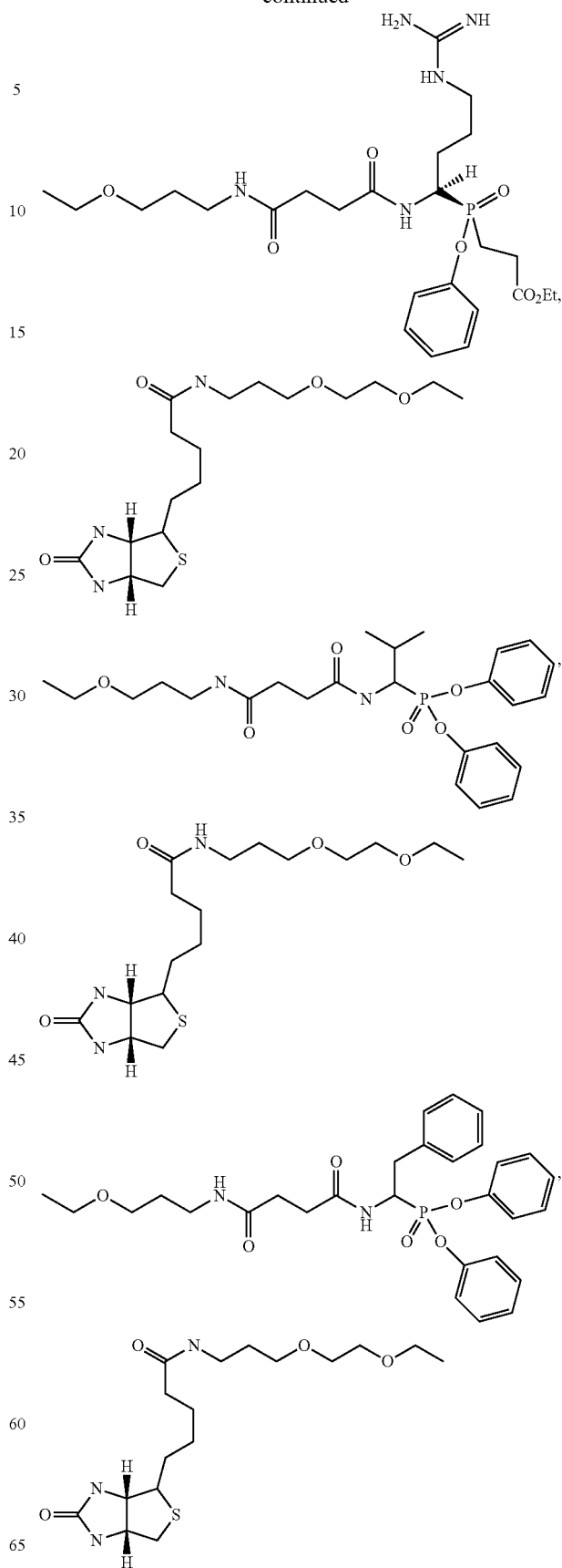

-continued

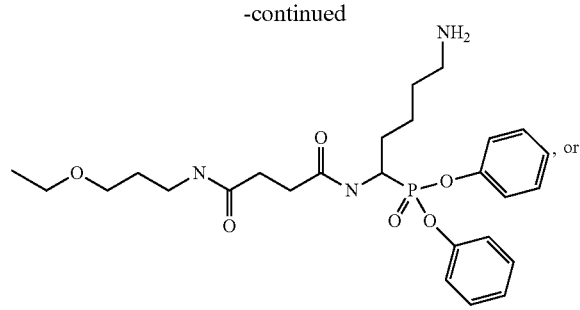

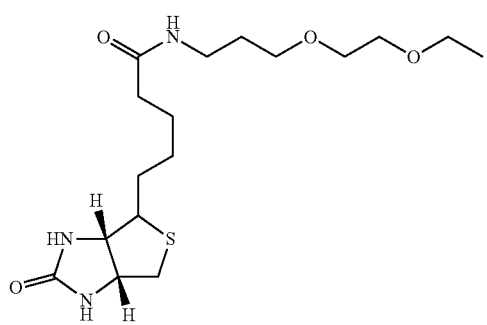

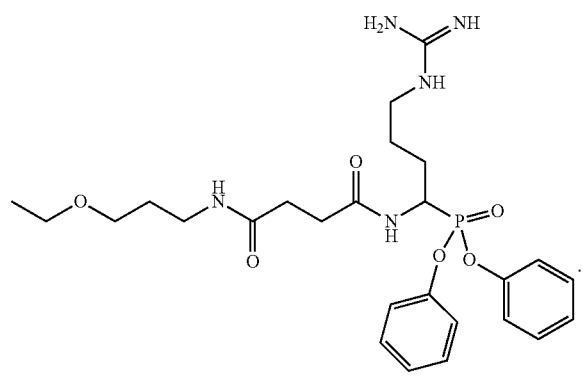

2. The compound of claim 1, wherein the compound is

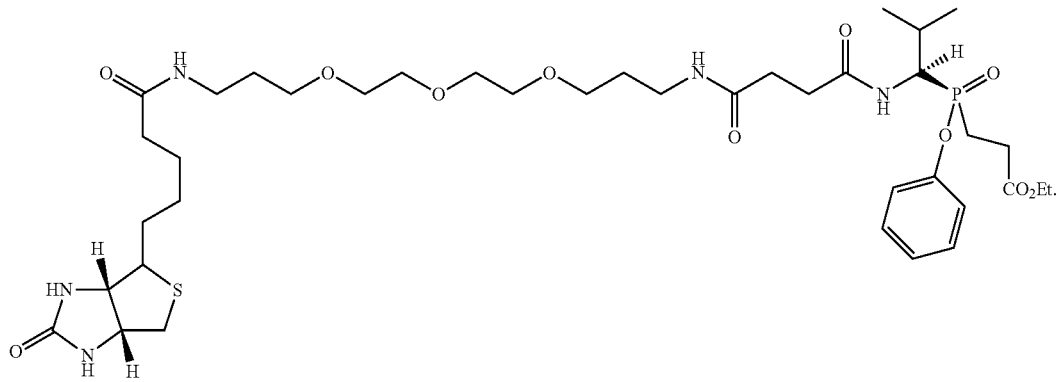 [SMILES: CCOC(=O)CC[P@@](=O)(Oc1ccccc1)[C@@H](NC(=O)CCC(=O)NCCCOCCOCCOCCCNC(=O)CCCCC1SC[C@@H]2NC(=O)N[C@H]12)C(C)C]

3. A method for the detection and/or inhibition of one or more proteases, comprising the steps of:
mixing a biological sample, with a compound as claimed in claim 1, allowing the compound to stably bind a target protease in the sample to form a detectable complex and detecting the detectable complex.

4. A method of detecting a pathological condition in a subject comprising the steps of:
providing a sample from the subject,
incubating the sample with a compound as claimed in claim 1 for binding a protease, in order to form a detectable complex and determining the amount of protease in the sample through comparison of the amount of the detectable complex present with a standard, and comparing the amount of protease in the sample with a normal level of protease in such a sample, wherein an elevated level of the protease compared to a normal level is indicative of a pathological condition.

5. The method as claimed in claim 4 wherein an increase of at least 5-100 fold is indicative of a pathological condition.

6. The method as claimed in claim 4 wherein the pathological condition is a chronic or acute airways disease such as cystic fibrosis, chronic obstructive pulmonary disease, bronchiectasis, congenital alphai antitrypsin, emphysema, acute respiratory distress (ARDS); athersoschlerosis; pancreatitis, acute periodontal disease, solid malignancies, disseminated intravascular dissemination, sepsis, aneurysms or chronic non-healing wounds, bacterial, viral or fungal infection.

7. An assay system for the detection of a protease comprising a compound as claimed in claim 1.

8. The assay system of claim 7 in the form of an ELISA assay, lateral flow device/dipstick or chip.

* * * * *